US Patent [19] Mitchell, III et al.

[11] 4,239,658
[45] Dec. 16, 1980

[54] CATALYSTS FOR THE CONVERSION OF RELATIVELY LOW MOLECULAR WEIGHT HYDROCARBONS TO HIGHER MOLECULAR WEIGHT HYDROCARBONS AND THE REGENERATION OF THE CATALYSTS

[75] Inventors: Howard L. Mitchell, III; Robert H. Waghorne, both of Baton Rouge, La.

[73] Assignee: Exxon Research & Engineering Co., Florham Park, N.J.

[21] Appl. No.: 27,246

[22] Filed: Apr. 5, 1979

Related U.S. Application Data

[63] Continuation-in-part of Ser. No. 903,814, May 8, 1978, Pat. No. 4,172,810.

[51] Int. Cl.$^3$ .................. B01J 21/04; B01J 23/10; B01J 23/58; B01J 23/64
[52] U.S. Cl. .................. 252/465; 252/416; 252/420; 252/462; 252/464; 252/468; 252/469; 585/417; 585/500; 585/656; 585/943
[58] Field of Search .............. 252/462, 464, 465, 468, 252/469, 416, 420; 585/417, 500, 656 R, 943

[56] References Cited
U.S. PATENT DOCUMENTS

| | | | |
|---|---|---|---|
| 2,447,016 | 8/1948 | Kearby | 208/136 X |
| 2,992,191 | 7/1961 | Erickson | 252/464 |
| 3,519,573 | 7/1970 | Coe | 252/420 X |
| 4,038,209 | 7/1977 | Schoofs | 252/416 X |
| 4,169,815 | 10/1979 | Drehman | 252/466 PT |

*Primary Examiner*—W. J. Shine
*Attorney, Agent, or Firm*—Llewellyn A. Proctor

[57] ABSTRACT

Novel regenerable catalyst-reagents, and a new and improved process utilizing said regenerable catalyst-reagents, for the conversion, and oligomerization of hydrocarbons, notably methane, at relatively low temperatures to produce products rich in ethylene or benzene, or both, usually in admixture with other hydrocarbons; and process for the regeneration of said catalyst-reagents. (a) The catalyst-reagents are multi-functional and are comprised of (1) a Group VIII noble metal having an atomic number of 45 or greater, nickel, or a Group I-B noble metal having an atomic number of 47 or greater; (2) a Group VI-B metal oxide which is capable of being reduced to a lower oxide, or admixture of metal oxides which includes one or more of such metal oxides; and, (3) a Group II-A metal selected from the group consisting of magnesium and strontium, composited with a suitably passivated, spinel-coated refractory support, notably an inorganic oxide support, preferably alumina; preferably calcium, composited with a suitably passivated, non-zinc containing spinel coated refractory support, notably an inorganic oxide support, preferably alumina.

39 Claims, No Drawings

CATALYSTS FOR THE CONVERSION OF RELATIVELY LOW MOLECULAR WEIGHT HYDROCARBONS TO HIGHER MOLECULAR WEIGHT HYDROCARBONS AND THE REGENERATION OF THE CATALYSTS

CROSS-REFERENCE TO RELATED APPLICATIONS

This is a continuation-in-part of Application Ser. No. 903,814 filed May 8, 1978; now U.S. Pat. No. 4,172,810.

BACKGROUND OF THE INVENTION AND PRIOR ART

It is the business of many refineries and chemical plants to obtain, process and upgrade relatively low value hydrocarbons to more valuable feeds, or chemical raw materials. For example, methane, the simplest of the saturated hydrocarbons, is often available in rather large quantities either as an undesirable by product in admixture with other more valuable higher molecular weight hydrocarbons, or as a component of an off gas from a process unit, or units. Though methane is useful in some chemical reactions, e.g., as a reactant in the commercial production of methanol and formaldehyde, it is not as useful a chemical raw material as most of the higher molecular weight hydrocarbons. For this reason process streams which contain methane are usually burned as fuel.

Methane is also the principal component of natural gas, which is composed of an admixture of normally gaseous hydrocarbons ranging $C_4$ and lighter and consists principally of methane admixed with ethane, propane, butane and other saturated, and some unsaturated hydrocarbons. Natural gas is produced in considerable quantities in oil and gas fields, often at remote locations and in difficult terrains, e.g., offshore sites, arctic sites, swamps, deserts and the like. Under such circumstances the natural gas is often flared while the oil is recovered, or the gas is shut in, if the field is too remote for the gas to be recovered on a commercial basis. The construction of pipelines to carry the gas is often not economical, due particularly to the costs of connecting numerous well sites with a main line. Transport of natural gas under such circumstances is also uneconomical because methane at atmospheric pressure boils at −258° F. and transportation economics dictate that the gas be liquefiable at substantially atmospheric pressures to reduce its volume. Even though natural gas contains components higher boiling than methane, and such mixtures can be liquefied at somewhat higher temperatures than pure methane, the temperatures required for condensation of the admixture is nonetheless too low for natural gas to be liquefied and shipped economically. Under these circumstances the natural gas, or methane, is not even of sufficient value for use as fuel, and it is wasted.

The thought of utilizing methane from these sources, particularly avoiding the tremendous and absolute waste of a natural resource in this manner, has challenged many minds; but has produced few solutions. It is highly desirable to convert methane to hydrocarbons of higher molecular weight than methane (hereinafter, $C_2+$) particularly admixtures of $C_2+$ hydrocarbon products which can be economically liquefied at remote sites; especially admixtures of $C_2+$ hydrocarbons rich in ethylene or benzene, or both. Ethylene and benzene are known to be particularly valuable chemical raw materials for use in the petroleum, petrochemical, pharmaceutical, plastics and heavy chemicals industries. Ethylene is thus useful for the production of ethyl and ethylene compounds including ethyl alcohol, ethyl ethers, ethylbenzene, styrene, ethylene oxide, ethylene dichloride, ethylene dibromide, acetic acid, polyethylene and the like. Benzene is useful in the production of ethylbenzene, styrene, and numerous other alkyl aromatics which are suitable as chemical and pharmaceutical intermediates, or suitable in themselves as end products, e.g. as solvents or high octane gasoline components.

It has been long known that methane, and natural gas could be pyrolytically converted to $C_2+$ hydrocarbons. For example, methane or natural gas passed through a porcelain tube at moderate red heat will produce ethylene and its more condensed homologues such as propylene, as well as small amounts of acetylene and ethane. Methane and natural gas have also been pyrolytically converted to benzene, the benzene usually appearing in measurable quantities at temperatures above about 1650° F., and perhaps in quantities as high as 6–10 wt. % at 2200° F. to 2375° F., or higher. Acetylene and benzene in admixture with other hydrocarbons, have been produced from methane and natural gas in arc processes, cracking processes, or partial combustion processes at temperatures ranging above about 2775° F. Heat for such reactions has been supplied from various sources including electrically heated tubes, electric resistance elements, and spark or arc electric discharges. These processes characteristically require considerable heat energy which, most often, is obtained from combustion of the by-product gases. The extreme temperatures make the operation of such processes uneconomical and, of course, serious materials problems are generally encountered. Numerous attempts have been made to catalyze these reactions at lower and more feasible temperatures, but such attempts have met with failure.

In all such processes of converting methane to $C_2+$ hydrocarbons a partial oxidation mechanism is involved, because hydrogen must be removed either as water, molecular hydrogen or other hydrogen-containing species. Likewise, any other polymerization mechanism wherein methane is converted to $C_2+$ hydrocarbon products requires a tremendous amount of energy, most often supplied as heat, to provide the driving force for the reactions. In the past the molecular hydrogen liberated by the reaction has often been separated and burned to provide the necessary process heat. This route has proven an abomination to the production of $C_2+$ hydrocarbons, but alternate reaction pathways have appeared little better, if any, for these have resulted in the production of large quantities of the higher, less useful hydrogen deficient polymeric materials such as coke, and highly oxidized products such as carbon dioxide and water.

It is nonetheless a primary objective of the present invention to obviate these and other prior art deficiencies and, in particular, to provide the art with novel catalysts, and a catalytic process for the production of higher molecular weight hydrocarbons from lower molecular weight hydrocarbons, especially for the production of $C_2+$ hydrocarbons from methane, natural gas, process streams rich in methane, and the like.

A specific object is to provide novel regenerable catalyst-reagents, and a new and improved process utilizing said regenerable catalyst-reagents, for the conversion, and oligomerization of methane at relatively low temperatures to higher molecular weight hydrocarbons, particularly products rich in ethylene or benzene, or both, usually in admixture with other hydrocarbons.

A yet more specific object is to provide novel regenerable catalyst-reagents, a novel and highly economic process for the low temperature catalytic conversion, and oligomerization, of natural gas to more easily liquefiable admixtures rich in $C_2+$ hydrocarbons, notably ethylene and benzene, which will make feasible the collection, liquefaction, shipment and use of much of the natural gas that is now flared and wasted at remote sites.

These and other objects are achieved in accordance with the present invention which embodies (a) novel multi-functional regenerable catalyst-reagents which are comprised of (1) a Group VIII noble metal having an atomic number of 45 or greater, nickel, or a Group I-B noble metal having an atomic number of 47 or greater (Periodic Table of the Elements; Sargent Welch Scientific Company, Copyright 1968), or admixture which includes one or more of said metals; (2) a Group VI-B metal oxide of the Periodic Table of the Elements which is capable of being reduced to a lower oxide, or admixture of metal oxides which includes one or more of such metal oxides; and, additionally (3) a Group II-A metal selected from the group consisting of magnesium and strontium, or admixture which includes one or more of such metals, composited with a suitably passivated, spinel-coated refractory support, notably an inorganic oxide support, preferably alumina; preferably calcium, composited with a suitably passivated, nonzinc containing spinel coated refractory support, notably an inorganic oxide support, preferably alumina;

(b) a novel hydrocarbon conversion process wherein a hydrocarbon feed, notably methane, or methane-containing gas, is contacted with a catalyst-reagent as characterized in (a), supra, at temperature ranging from about 1150° F. to about 1600° F., preferably from about 1250° F. to about 1350° F., at sub-atmospheric, atmospheric, or supra atmospheric pressure sufficient to react and form $C_2+$ hydrocarbons; and (c) a process for regeneration of said catalyst-reagent which has become inactivated as by use in the process characterized in (b), supra, by contact thereof in an exothermic reaction with water, oxygen or an oxygen-containing gas, preferably air, at temperatures sufficient to reoxidize the Group VI-B metal oxide, or metal oxides, and preferably also sufficient to provide the required sensible heat to said novel hydrocarbon conversion process (b), supra, on recycle of the catalyst-reagent; which suitably ranges from about 1000° F. to about 1600° F., preferably from about 1250° F. to about 1450° F., carbon dioxide and water being released in the regeneration reaction.

The novel catalyst-reagents are multi-functional and, though the exact nature of the reaction paths are by no means certain, the included components are believed to play different mechanistic functions in the production of oligomers from the low molecular weight hydrocarbon feeds, notably methane. The Group I-B (silver, gold) or VIII (rhodium, palladium, osmium, iridium and platinum) noble metal, or nickel, the first essential component, of which the Group VIII noble metals, notably platinum, iridium and palladium, but particularly platinum, are preferred, is believed to enter into a dissociative chemisorption reaction with the hydrocarbon feed and cause it to lose hydrogen. For example, in the reaction with methane, the Group I-B or Group VIII noble metal, or nickel, functions to cause dissociative chemisorption of the methane onto the surface of the catalyst to produce species which can react to form ethylene directly, another species which reacts to form ethane and higher molecular weight aliphatic hydrocarbons, or both, and other species which can directly react with the Group VI-B metal oxide to form water.

The Group VI-B metal oxide, the second essential component, is characterized as an oxide which is capable of being reduced in the reaction to a lower oxide or the zero valent metal, or both. The reducible Group VI-B metal oxide component, comprising an oxide, or oxides, of the multivalent metals chromium, molybdenum and tungsten, is believed to provide a catalytic function, in addition to the reagent function which is a function of the change of oxidation state of the metal. Thus, it acts as a reagent in that it is believed to donate oxygen for reaction with abstracted hydrogen to form water and thereby provide the energy necessary to sustain the reaction. In its catalytic function, it is believed that the low valence oxides of the Group VI-B metal, or the completely reduced metal, provide a cyclization function whereby acetylene, acetylides and the like, and perhaps even ethylene are converted into aromatics, notably benzene. Thus, it is one or more of the products of the reagent function of the Group VI-B metal oxide components which are believed to provide the catalytic function of the Group VI-B metals.

It has also been found that the activity of the Group VI-B reducable metal oxide to react with abstracted hydrogen and form water can be supplemented, or enhanced, by the additional presence of oxides of (i) Group III-A metals having an atomic number of 31 or greater (gallium, indium and thallium), (ii) Group IV-B transition metals of atomic number ranging from 22 to 40 (titanium and zirconium), (iii) Group V-B transition metals (vanadium, niobium and tantalum), (iv) Group VII-B transition metals (manganese and rhenium), (v) Group VIII nonnoble metals of atomic number ranging from 26 to 27 (iron and cobalt), (vi) metals of the lanthanum series of atomic number ranging from 58 to 71 (cerium, praseodymium, neodynium, samarium, europium, gadolinium, terbium, dysprosium, holmium, erbium, thulium, ytterbium, lutetium), and (vii) metals of the actinum series of atomic number ranging from 90 to 92 (thorium and uranium). Of these, the preferred oxygen donor compounds comprise the oxides of vanadium, niobium, rhenium, cerium and uranium.

The Group II-A, or alkaline-earth metals (magnesium, strontium, and calcium), of which calcium is preferred, constitute the third essential component of the catalyst. The Group II-A metal is put on the catalyst support as an oxide and, in performing its function, is believed to form a Group II-A metal carbide, or carbides as intermediates during the course of the reaction. This, of course, does not suggest that other species containing the Group II-A metal are not formed, and possibly active during the reaction. However, in an initial stage it is believed that the oxide of the Group II-A metal supplies oxygen which reacts with abstracted hydrogen to form water, thus providing some of the energy for the reaction. Calcium is believed to function particularly well in this aspect. The Group II-A metal carbides, particularly carbides of the heavier Group II-A metals, are also believed to form compounds which possess carbon-carbon bonds, or polycarbon-carbides, particularly $C_2$ species or acetylides, which are thought to be intermediates, or precursors of intermediates, in the formation of cyclic compounds.

It is also essential in formation of these catalysts that the several components be composited with a passivated surface, spinel-coated inorganic metal oxide support, preferably a spinel-coated alumina upon which the several components are sequentially impregnated, or coimpregnated by any of the common techniques in use for the preparation of heterogeneous catalysts. The term "spinel," as used herein, designates a binary oxide which is characterized as having either a normal or inverse spinel structure. The normal spinel structure can be represented by the formula $MY_2O_4$ wherein M and Y are cations of different metals, and the inverse spinel structure can be represented by the formula $Y(X-Y)O_4$ wherein Y and X are cations of different metals. The sum of the cationic charges of a spinel, whether normal or inverse, is equal to 8. A description of the spinel-type structures is found in Structural Inorganic Chemistry, A. F. Wells, 3rd Edition, Oxford, the Clarendon Press, 1962, at pages 487–488, herewith incorporated by reference.

While calcium is the preferred Group II-A reagent metal it is nonetheless essential that calcium reagent not be employed in the presence of zinc. This is true even when the zinc is present as a constituent or part of the passivated, spinel-coated surface, e.g., as when the calcium is deposited on a zinc aluminate spinel carrier, or zinc aluminate spinel coated support. The presence of zinc, among other things, causes the formation of considerable amounts of coke with drastic reduction in the formation of the desired products.

Thermodynamic considerations of the possible reaction paths leave little doubt but that numerous possible reaction paths favor the formation of a considerable amount of coke and/or carbon dioxide, with little or no yield of potentially valuable products, a conclusion which fits well with the results of many past experiments. However, pursuant to the practice of this invention, albeit some coke, polymeric, or carbonaceous material is produced, essentially all of this material that is formed in the reaction is burned to carbon dioxide and fully utilized in the regeneration stage to provide process heat. On the other side of the process, relatively little carbon dioxide is formed in the reactions taking place in the main reactor. It has been demonstrated that the catalyst-reagents of this invention, under the desired conditions for conducting the process, produce products containing an admixture of valuable oligomers, particularly ethylene and benzene.

Though the exact nature of the reaction paths is by no means certain, as suggested, it is believed that the Group I-B noble metals and Group VIII noble metals, inclusive of nickel, function to cause one or more dissociative chemisorptions of the methane onto the surface of the catalyst to produce species which may react to form ethylene directly, or another species which may react to form ethane and higher molecular weight aliphatic hydrocarbons, or both, and another species such as adsorbed hydrogen, which may react directly with the transition metal or other oxide to form water. Or such species may react with the Group II-A carbides to liberate ethylene, form acetylene, or other products, form intermediates which lead to cyclization, or react with cyclization or polymerization products to form benzene or other products which appear in the exit gases from the reactor. The Group VI-B metal oxide also may react directly with abstracted or liberated hydrogen to form water, and by interaction with a Group I-B noble metal or Group VIII noble metal, or nickel, is believed to form water and a species which further reacts to form ethylene. Where methane is used as a feed, it is thus envisioned that the reaction mechanisms with a multivalent Group I-B noble metal or Group VIII noble metal, or nickel, referred to as "M", may include the following sequences of reactions, to wit:

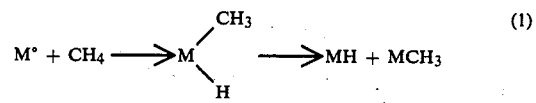

(2) $2MCH_3 \rightarrow 2M° + H_3C-CH_3$ (2)

(3) $MCH_3 + M° \rightarrow M=CH_2 + MH$ (3)

(4) $2M=CH_2 \rightarrow 2M° + H_2C=CH_2$ (4)

and,

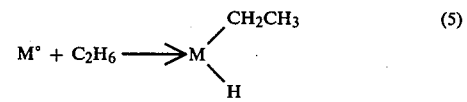

It is also envisioned that the multivalent transition metal oxide, $M'O_n$, the transition metal being designated as M', the oxygen as O, with the subscript n representing the number of oxygen atoms associated with M', or the ratio of oxygen atoms to M atoms in the association since n need not be an integer, reacts with the intermediate MH [Equation (1), supra] as follows:

$$2MH + M'O_n \rightarrow M° + M'O_{n-1} + H_2O \qquad (6)$$

and with abstracted and liberated hydrogen as follows;

$$M'O_n + H_2 \rightarrow M'O_{n-1} + H_2O \qquad (7)$$

and, M' participates with M in reacting with methane, as follows:

(8) $M'O_n + CH_4 + M° \rightarrow M'O_{n-1} + H_2O + M=CH_2$ (8)

Likewise, $MO_{n-1}$ and $M'O_{n-1}$ can further react in similar manner to produce additional water, ethylene, ethane, and other hydrocarbons until the valence of M, M' and M" have been reduced to some lower level or to zero, at which time further reactions such as described are no longer possible without reoxidation of the catalyst by regeneration.

The presence of the Group II-A metal, or alkaline earth metal component, favors the production of larger amounts of benzene in the products of the reaction. In this type of reaction, it is believed that the methane or organometallic intermediates interact with the Group II-A metal component to form metal carbides and water. The carbides, acetylides, propadiynides and the like, it is believed, react in turn with the water or abstracted or liberated hydrogen to generate benzene, ethylene, and/or the other products of the process.

It is known that acetylene can be trimerized at certain conditions to yield benzene, but it is also known that free acetylene also has a propensity to react to form coke; which form of reaction is highly undesirable. Such reaction can thus be represented by the following equation, to wit:

$$C_2H_2 \rightarrow Heat + (C_2)_x + H_2 \text{ (or Coke} + H_2) \quad (9)$$

In the catalytic reaction of this invention, however, it is not believed that free acetylene is formed and whereinafter $C_2H_2$ is represented in the equation, the acetylene is believed present only as a transient, or molecular species complexed with one or more metal atoms, and which is rapidly converted into benzene, ethylene or other hydrocarbon or coke. Therefore, it is theorized that the reaction pathway to the formation of benzene may be shown by equations 10–16, infra. Representing a Group II-A metal as M″, and a carbide, acetylide, or the like of such metals as M″$_m$C, M″$_m$C$_2$, M″$_m$C$_3$, the designations denoting the degree of association of carbon/carbide atoms within the material, all of which generally fit in the "metal carbide" category, and the subscripts denoting generally the number of metal atoms associated with each carbide anion carbon or group of carbons, the following reactions are believed to occur in forming the carbides, acetylides, to wit:

$$2M''O + CH_4 \rightarrow M''_2C + 2H_2O \quad (10)$$

$$M''_2C, M''C, \text{etc.} \rightarrow M''C_2, M''C_3, M''_2C_3, \text{etc.} \quad (11)$$

The acetylene forming reaction is representing by the following equation, to wit:
$$M''C_2 + H_2O \rightarrow M''O + C_2H_2 \quad (12)$$

The acetylene trimerization may be represented by the following equation:
$$3C_2H_2 + \text{Catalyst} \rightarrow C_6H_6 + \text{Catalyst} \quad (13)$$

Where the catalyst is M′° or lower valent M′O$_z$ and a similar sort of dimerization of C$_3$ materials is likewise possible. An alternate more likely cyclization route can also take place, directly from the carbide, to wit:

$$3M''C_2 + M'O_2 \rightarrow 2M''O + M'C_6, \text{ etc.} \quad (14)$$
$$M'C_6 + 6MH \rightarrow 6M^* + M'° + C_6H_6 \quad (15)$$
$$2M''C_3 + M'O_2 \rightarrow 2M''O + M'C_6 \quad (16)$$
$$M'C_6 + 6CH_4 + 6M° \rightarrow M' + 6MCH_3 + C_6H_6 \quad (17)$$

Another alternate pathway for the cyclization to benzene involves the dehydrogenation and cyclization of three ethylenes via reactions on the M and M′ catalyst and reagent metals.

However, it is also possible that the reaction pathway to $C_2^+$ hydrocarbons, inclusive of ethylene and benzene may be through the catalytic or thermal formation of a particular type of "coke" which catalytically or thermally decomposes in the reaction to form the thermally stable volatile products, benzene and ethylene, to wit:

$$CH_4 + \text{Catalyst} \rightarrow \text{"Coke"} + \text{Catalyst} + H_2O \quad (18)$$

$$\text{"Coke"} + \text{Catalyst } (+2CH_4) \rightarrow \text{Coke} + C_2H_4 + C_6H_6 \quad (19)$$

The catalyst or feed, or both, may be furnishing hydrogen to decompose the "Coke" as, to wit:
$$M^* + CH_4 \rightarrow MH + \text{"Coke"} \quad (20)$$

$$MH + \text{"Coke"} \rightarrow M^* + C_2H_4 + C_6H_6 \quad (21)$$

In the preparation of the catalyst-reagents, a porous metal oxide support, preferably one which has been desurfaced by contact with steam, is first passivated and the surface thereof converted to a spinel. This is accomplished by treatment of the support with at least one metal component (other than zinc when calcium is to be deposited on the support), preferably a metal from Group II-A, such that the sum of the ionic charges of the metal of the metal oxide support and the metallic element, or metallic elements, of the metal component used to treat the support satisfy the requirement for spinel formation, i.e., that the sum of the valences equals 8 and the ionic radii of the metals satisfy the requirements for formation of the normal or inverse spinel type structures. Exemplary of materials which can be used as supports are magnesium oxide, titanium oxide, zirconium oxide, hafnium oxide, and the like, preferably alumina. Suitably, the metal oxide support, preferably one having an initial surface area ranging from about 50 m$^2$/g to about 250 m$^2$/g, preferably above 150 m$^2$/g, is treated by contact, and impregnation with a solution of a compound of the desired metal component which is deposited on the metal oxide support. The treated or impregnated metal oxide is subsequently calcined, suitably at a temperature ranging from about 925° F. to about 1825° F., this producing a surface spinel or spinel-coating on the metal oxide support. The spinel surfaced support is then treated with a solution, or solutions, containing compounds which provide the essential substituents characterized in (a), supra.

The several components are deposited on the passivated, spinel-coated support by the impregnation method. Pursuant to this method, a compound, or compounds which contain the desired metal, or metals, are dissolved in solution in the desired concentration. The support in solvated, dry or calcined state is contacted with the metal or metals-containing solution, or solutions, and thereby impregnated by either the so-called "incipient wetness" technique, or technique embodying absorption from a dilute solution, or solutions, with subsequent drying of the support. In the impregnation procedure, the Group II-A metal is generally first impregnated onto the passivated, spinel-coated support; the amount added to the support being additional to any such similar or dissimilar metal which may have been used to form the spinel-coating, since that used in forming the spinel is not contained thereon in active form. The Group II-A metal impregnated support is then, preferably, calcined in an inert or oxidizing atmosphere and the Group VI-B metal is then impregnated onto the support, and again calcined. Suitably also, compounds of the Group II-A and VI-B metals can be coimpregnated onto the passivated, spinel-coated surface and the support then dried and calcined. It is essential, in either event, after deposition of the Group VI-B metal to calcine the catalyst-reagent in an oxidizing atmosphere, i.e., in the presence of air or an oxygen-containing gas, to convert the Group VI-B metal to an oxide. The Group III-A, and transition metals of IV-B, V-B, VII-B, inclusive also of the lanthanide and actinium series metals, and iron and cobalt, alone or in admixture with other metals are similarly impregnated onto the support and the impregnated support calcined in an oxidizing atmosphere to form an oxide, or oxides of the metal. The Group I-B or Group VIII noble metal, or nickel, is generally impregnated onto the passivated, spinel-coated support after deposition of the other essential components and then calcined, suitably in air; or added by coimpregnation with one or more of the other essential or non-essential components. Where the impregnating compound contains halogen, or other undesirable component, wet calcination may be employed to remove the halide from the catalyst-reagent. In all embodiments, the support can be treated by contact with a single solution containing the desired amounts of a metal, or metals, or treated sequentially by contact with a solution containing one metal, and then with a solution which contains another metal, or metals, in the desired amounts. Large particles, whether pilled, pelleted, beaded or extruded, can be so-treated and then crushed to the desired size, or the particle can be pre-reduced in size, and then treated. The catalyst-reagent, in either instance, can then be dried, calcined and then contacted as fixed, fluidized or moving bed with the feed at the desired reaction conditions.

In the preparation of the catalyst-reagents the Group I-B or Group VIII noble metals, or nickel, is deposited on the support in concentration ranging from about 0.01 percent to about 2 percent, preferably from about 0.1 to about 1 percent, calculated as metallic metal based on the weight of the total catalyst-reagent (dry basis). The reducable Group VI-B metal oxide is deposited on the catalyst-reagent in concentration sufficient to supply at least one-half of an atom of oxygen for each hydrocarbon molecule which is to be oligomerized, and preferably at least one atom of oxygen for each hydrocarbon which is to be oligomerized. Generally, at least about 1.1:1 to at least 1.5:1 atoms of oxygen are supplied for each molecule of methane when high ethylene content is desired in the product. At least 1.5:1 atoms of oxygen are supplied for each molecule of methane when high benzene content is desired in the product. The Group VI-B metal is deposited on the catalyst-reagent in concentration ranging from about 1 percent to about 20 percent, preferably from about 3 percent to about 10 percent, calculated as metallic metal based on the weight of the total catalyst-reagent (dry basis). Suitably also the oxides of the Group III-A metals, the oxides of the Group IV-B, V-B, VII-B transitional metals, the oxides of iron, cobalt and the oxides of the metals of the lanthanide and actinide series are deposited on the catalyst in concentration ranging from about 0.01 percent to about 25 percent, preferably from about 5 percent to about 15 percent calculated as metallic metal based on the weight of the total catalyst-reagent (dry basis). The oxide of the Group II-A, or alkaline earth metal is deposited on the catalyst-reagent in concentration ranging from about 1 percent to about 30 percent, preferably from about 5 percent to about 25 percent calculated as metallic metal based on the weight of the total catalyst-reagent (dry basis). In compositing these metals with the catalyst-reagent, the Group II-A metal is composited in an amount sufficient to provide an atomic ratio of at least about 3:1 relative to the Group VI-B metal, and preferably the ratio of the Group II metal/Group VI-B metal ranges from about 3:1 to about 40:1, preferably from about 5:1 to about 12:1 when a relatively high concentration of benzene is desired in the product.

The catalyst-reagent, particularly in view of its dual role as reagent and catalyst, eventually loses its activity and its activity must be restored. Restoration of the activity of the catalyst-reagent is performed by oxidative regeneration, i.e., by contact of the catalyst-reagent with water, oxygen or oxygen-containing gas, preferably air, at temperatures sufficiently elevated to burn off accumulated coke and reoxidize the Group VI-B metals and Group II-A metals; as well as the metals of Groups III-A, IV-B, V-B, VII-B, iron, cobalt and the lanthanides and actinides, to the extent they are present in the catalyst-reagent. Temperatures on the order of about 700° F. are generally adequate to reoxidize these metals and restore the activity of the catalyst-reagent, but preferably temperatures on the order of about 1000° F. to about 1600° F., more preferably from about 1250° F. to about 1450° F., are employed in the regeneration zone and the hot regenerated catalyst-reagent is recycled to the hydrocarbon reaction zone in quantity sufficient to supply the sensible heat needed for the reaction. Generally, adequate heat is maintained by burning the coke from the catalyst-reagent during the regeneration. Pressure, while not critical, is generally maintained above atmospheric, suitably between atmospheric and about 20 atmospheres.

The invention will be more fully understood by reference to the following non-limiting examples which illustrate its more salient features. All parts are in terms of weight except as otherwise specified.

EXAMPLES

Catalyst-reagents were prepared from spinel blocked alumina supports made by impregnating via the incipient wetness technique a commercially available, high purity gamma alumina calcined at 1000° F. for two hours to produce an alumina having a surface area of 193 m$^2$/g (B.E.T.) with an aqueous solution of a salt of the blocking metal. For example, in the preparation of a $CaAl_2O_4$ spinel blocked alumina support, as for catalyst-reagent F, a calcium nitrate solution was formed by dissolving magnesium nitrate in water, and the calcium solution was then added to the support in amount calculated to deposit 3.5 percent Ca onto the support. The impregnated support was dried, and then subjected to a subsequent calcination at 1000° F. for four hours, and at 1300° F. for an additional hour. The $CaAl_2O_4$ spinel blocked alumina support was then impregnated with an aqueous solution of a salt of the desired Group II-A metal, e.g., calcium nitrate, as in the preparation of Catalyst F, and calcined for 4 hours at 1000° F. Impregnation was also via the incipient wetness technique with subsequent calcination, alternate impregnations and calcinations having been conducted a number of times in sequence to bring the Group II-A metal concentration to the desired concentration. After the final calcination, a Group VI-B metal, Cr was deposited from a solution of a salt of the Group VI-B metal onto the catalyst-reagent to provide the desired Group VI-B metal concentration after calcination for 4 hours at 1000° F. with subsequent calcination in air at 1300° F. for 1 hour. The calcined catalyst-reagent was then impregnated by adsorption from dilute solution with an acid salt of the Group VIII noble metal, e.g., a hexachloroplatinic acid, $H_2PtCl_4$, solution sufficient to provide the desired concentration of platinum on the catalyst-reagent, and again calcined for 16 hours in air at 1300° F.

A 5 gram portion of each catalyst was charged into a quartz tube furnace and heated slowly at essentially ambient pressure with a flowing stream of nitrogen over a period of 6 hrs. to 1300° F. The flow of nitrogen was then discontinued, and then a stream of essentially pure methane (99.4%) was passed across the catalyst-reagent for 30 minutes. The flow of methane was then discontinued and nitrogen was again introduced, the nitrogen having been substituted at the end of this period to act as a carrier gas. The entire effluent was collected in a neoprene rubber bag during the time that hydrocarbons were evolved from the system. A sample of the collected product was then subjected to a mass spectrometric gas analysis to determine the hydrocarbon components present in the gaseous product in significant quantity, and the amount of coke deposited on the catalyst was measured.

The results obtained are given in Table I below:

TABLE I
TESTING OF CATALYST REAGENTS FOR METHANE POLYMERIZATION

| Test Run Number | 7 | 8 | 9 | 10 |
|---|---|---|---|---|
| Catalyst Designation | E | F | $F_2$ | G |
| Nominal Catalyst Type | CaCrPt | CaCrPt | CaCrPt | CaMoVPt |
| Use | Original[1] | Original[1] | Regenerated[2] | Original[1] |
| Base Material $M''''_m O_n$ | $\gamma$-$Al_2O_3$ | $\gamma$-$Al_2O_3$ | $\gamma$-$Al_2O_3$ | $\gamma$-$Al_2O_3$ |
| Blocking Metal $M''''$ | Zn | Ca[3] | Ca[3] | Ca[3] |
| Concentration Blocking Metal $M''''$ (Wt. %) | 5.7 | 3.5 | 3.5 | 3.4 |
| Metal M | Pt | Pt | Pt | Pt |
| Concentration M (Wt. %) | 0.2 | 0.2 | 0.2 | 0.3 |
| Metal M' | Cr | Cr | Cr | Mo |
| Concentration M' (Wt. %) | 3.8 | 3.8 | 3.8 | 7.0 |
| Metal M'' | Ca | Ca | Ca | Ca |
| Concentration M'' (Wt. %) | 8.3 | 8.3 | 8.3 | 9.2 |
| Metal M''' | — | — | — | V |
| Concentration M''' (Wt. %) | 0.0 | 0.0 | 0.0 | 10.2 |
| Product Analysis Component (Mole %) | | | | |
| $CH_4$ | 63.24 | 39.93 | 46.20 | 44.75 |
| $C_2H_2$ | — | — | — | 0.03 |
| $C_2H_4$ | 0.03 | 2.33 | 2.87 | 3.64 |
| $C_2H_6$ | 0.16 | 0.38 | 0.46 | 0.19 |
| $C_3H_6$ | — | — | — | 0.02 |
| $C_3H_8$ | — | 0.01 | — | 0.00 |
| $C_4H_8$ | 0.005 | — | 0.01 | 0.00 |
| n-$C_4H_{10}$ | 0.01 | — | 0.02 | 0.01 |
| $C_6H_6$ | 0.00 | 2.14 | 2.46 | 1.99 |
| $N_2$ | 36.55 | 55.21 | 47.98 | 49.37 |
| Product Composition Component (Wt. %) | | | | |
| $CH_4$ | 49.61 | 26.34 | 31.23 | 30.34 |
| $C_2H_2$ | — | — | — | 0.03 |
| $C_2H_4$ | 0.04 | 2.69 | 3.39 | 4.32 |
| $C_2H_6$ | 0.24 | 0.47 | 0.58 | 0.24 |
| $C_3H_6$ | — | — | — | 0.04 |
| $C_3H_8$ | — | 0.02 | — | 0.00 |
| $C_4H_8$ | 0.01 | — | 0.02 | 0.01 |
| n-$C_4H_{10}$ | 0.03 | — | 0.05 | 0.02 |
| $C_6H_6$ | 0.00 | 6.87 | 8.10 | 6.57 |
| $N_2$ | 50.07 | 63.60 | 56.63 | 58.44 |
| Coke on Catalyst (Wt. %)[4] | 28.73 | 2.48 | 2.16 | 1.74 |
| Coke on Catalyst After Regeneration (Wt. %)[6] | 0.24 | 0.11 | 0.22 | 0.16 |

[1] Original catalysts used in first cycle of methane polymerization.
[2] $F_2$ Catalyst F once regenerated, used in the second cycle of methane polymerization.
[3] Concentration of blocking reagent metal $M''''$ used for spinel formation is not included as part of $M''$ concentration even though the identical metal was used for both purposes.
[4] "Coke on Catalyst" may also include significant quantities of metal carbide "carbon."
[5] Testing at 1 atm. pressure, pure $CH_4$ feed, $N_2$ purge before and after, 0.5 hrs/run except first cycle on B above at 4.0 hrs.
[6] Regeneration by final 700° C. air burning.

From these data it will be observed that catalysts which contain the Group II-A metal catalyst component, except where zinc is present (Test Run Number 7), are quite effective in oligomerizing methane to produce product compositions rich in ethylene and benzene. Where zinc is present, however, a major amount of the methane is converted to coke, with minimal production of $C_2^+$ gases.

It is apparent that various modifications and changes can be made without departing the spirit and scope of the invention.

What is claimed is:

1. A multi-functional regenerable catalyst-reagent composition suitable for the oligomerization of hydrocarbons which comprises (1) a Group VIII noble metal having an atomic number of 45 or greater, nickel, or a Group I-B noble metal having an atomic number of 47 or greater, (2) a Group VI-B metal oxide which is capable of being reduced to a lower oxide, and (3) a Group II-A metal selected from the group consisting of magnesium and strontium, composited with a spinel-coated refractory support, or calcium composited with a non-zinc containing spinel-coated refractory support.

2. The composition of claim 1 wherein the Group VIII noble metal is platinum, iridium or palladium.

3. The composition of claim 1 wherein the Group VI-B metal is chromium, molybdenum or tungsten.

4. The composition of claim 1 wherein the Group II-A metal is calcium.

5. The composition of claim 1 wherein the spinel-coated inorganic oxide is alumina.

6. The composition of claim 1 wherein the Group VIII noble metal is platinum, the Group VI-B metal is chromium, molybdenum or tungsten, and the Group II-A metal is calcium.

7. The composition of claim 1 wherein the Group VIII noble metal is platinum, the Group VI-B metal is chromium, molybdenum or tungsten, the Group II-A metal is calcium, and the support is alumina.

8. The composition of claim 1 wherein the catalyst-reagent composition contains additionally a Group III-A metal having an atomic number of 31 or greater, a IV-B, V-B or VII-B transition metal, iron, cobalt, or a metal of the actinide or lanthanide series.

9. The composition of claim 1 wherein the Group VIII noble metal is platinum, the Group VI-B metal is chromium, molybdenum or tungsten, the Group II-A metal is calcium, the support is alumina, and the catalyst-reagent composition contains additionally a Group III-A metal having an atomic number of 31 or greater, a IV-B, V-B or VII-B transition metal, iron, cobalt, or a metal of the actinide or lanthanide series.

10. A process for the regeneration of a catalyst-reagent which has become inactivated in a hydrocarbon conversion reaction which comprises
contacting said catalyst-reagent comprising (1) a Group VIII noble metal having an atomic number of 45 or greater, nickel, or a Group I-B noble metal having an atomic number of 47 or greater, (2) a Group VI-B metal oxide which is capable of being reduced to a lower oxide, and (3) a Group II-A metal selected from the group consisting of magnesium and strontium, composited with a spinel-coated refractory support, or calcium composited with a non-zinc containing spinel-coated refractory support with water, oxygen or an oxygen-containing gas
at temperatures ranging from about 1000° F. to about 1600° F.

11. The process of claim 10 wherein the Group VIII noble metal is platinum, iridium or palladium.

12. The process of claim 10 wherein the Group VI-B metal is chromium, molybdenum or tungsten.

13. The process of claim 10 wherein the Group II-A metal is calcium.

14. The process of claim 10 wherein the spinel-coated inorganic oxide is alumina.

15. The process of claim 10 wherein the Group VIII noble metal is platinum, the Group VI-B metal is chromium, molybdenum or tungsten, and the Group II-A metal is calcium.

16. The process of claim 10 wherein the Group VIII noble metal is platinum, the Group VI-B metal is chromium, molybdenum or tungsten, the Group II-A metal is calcium, and the support is alumina.

17. The process of claim 10 wherein the catalyst-reagent composition contains additionally a Group III-A metal having an atomic number of 31 or greater, a IV-B, V-B or VII-B transition metal, iron, cobalt, or a metal of the actinide or lanthanide series.

18. The process of claim 10 wherein the Group VIII noble metal is platinum, the Group VI-B metal is chromium, molybdenum or tungsten the Group II-A metal is calcium, the support is alumina, and the catalyst-reagent composition contains additionally a Group III-A metal having an atomic number of 31 or greater, a IV-B, V-B or VII-B transition metal, iron, cobalt, or a metal of the actinide or lanthanide series.

19. The process of claim 10 wherein the catalyst-reagent contains coke deposits, and coke is burned from the catalyst to generate process heat.

20. The composition of claim 1 wherein the Group VIII noble metal, nickel or Group I-B noble metal is deposited on the support in concentration ranging from about 0.01 percent to about 2 percent, calculated as metallic metal based on the weight of the total catalyst-reagent.

21. The composition of claim 20 wherein the Group VIII noble metal, nickel or Group I-B noble metal is deposited on the support in concentration ranging from about 0.1 percent to about 1 percent.

22. The composition of claim 1 wherein the Group VI-B metal oxide is deposited on the catalyst-reagent in concentration ranging from about 1 percent to about 20 percent calculated as metallic metal based on the weight of the total catalyst-reagent.

23. The composition of claim 1 wherein the Group VI-B metal oxide is deposited on the catalyst-reagent in concentration ranging from about 3 percent to about 10 percent.

24. The composition of claim 1 wherein the Group II-A metal is deposited on the catalyst-reagent in concentration ranging from about 1 percent to about 30 percent calculated as metallic metal based on the weight of the total catalyst-reagent.

25. The composition of claim 24 wherein the Group II-A metal is deposited on the catalyst-reagent in concentration ranging from about 5 percent to about 25 percent.

26. The composition of claim 22 wherein the Group II-A metal is provided in atomic ratio of at least about 3:1 relative to the Group VI-B metal.

27. The composition of claim 26 wherein the Group II-A metal is provided in atomic ratio of at least about 3:1 to about 40:1.

28. The composition of claim 27 wherein the Group II-A metal is provided in atomic ratio of at least about 5:1 to about 12:1.

29. The composition of claim 1 wherein the Group VIII noble metal is platinum, the Group VI-B metal is chromium, molybdenum or tungsten, the Group II-A metal is magnesium, strontium or calcium, and the support is magnesium oxide, titanium oxide, zirconium oxide or hafnium oxide.

30. The process of claim 10 wherein the Group VIII noble metal, nickel or Group I-B noble metal is deposited on the support in concentration ranging from about 0.01 percent to about 2 percent, calculated as metallic metal based on the weight of the total catalyst-reagent.

31. The process of claim 30 wherein the Group VIII noble metal, nickel or Group I-B noble metal is deposited on the support in concentration ranging from about 0.1 percent to about 1 percent.

32. The process of claim 10 wherein the Group VI-B metal oxide is deposited on the catalyst-reagent in concentration ranging from about 1 percent to about 20 percent calculated as metallic metal based on the weight of the total catalyst-reagent.

33. The process of claim 30 wherein the Group VI-B metal oxide is deposited on the catalyst-reagent in concentration ranging from about 3 percent to about 10 percent.

34. The process of claim 10 wherein the magnesium, strontium or calcium is deposited on the catalyst-reagent in concentration ranging from about 1 percent to about 30 percent calculated as metallic metal based on the weight of the total catalyst-reagent.

35. The process of claim 34 wherein the magnesium, strontium or calcium is deposited on the catalyst-reagent in concentration ranging from about 5 percent to about 25 percent.

36. The process of claim 32 wherein the magnesium, strontium or calcium is provided in atomic ratio of at least about 3:1 relative to the Group VI-B metal.

37. The process of claim 36 wherein the magnesium, strontium or calcium is provided in atomic ratio of at least about 3:1 to about 40:1.

38. The process of claim 37 wherein the magnesium, strontium of calcium is provided in atomic ratio of at least 5:1 to about 12:1.

39. The process of claim 10 wherein the Group VIII noble metal is platinum, the Group VI-B metal is chromium, molybdenum or tungsten, the Group II-A metal is magnesium, strontium or calcium, and the support is magnesium oxide, titanium oxide, zirconium oxide or hafnium oxide.

* * * * *